Figure 1:

United States Patent

Zenka et al.

[11] Patent Number: 5,096,930
[45] Date of Patent: Mar. 17, 1992

[54] PREPARATION OF THE IMPROVEMENT OF THE REGENERATIVE PROCESS OF INJURED STRIATED MUSCLES

[75] Inventors: Jan Ženka, České Budějovice; Dagmar Hulínská; Radim Holuša, both of Prague; Theodor Pokorny; Alexandr Jegorov, both of České Budejovice, all of Czechoslovakia

[73] Assignee: Ceskoslovenska akademie ved, Prague, Czechoslovakia

[21] Appl. No.: 437,371

[22] Filed: Nov. 15, 1989

[30] Foreign Application Priority Data

Nov. 22, 1988 [CS] Czechoslovakia .................. 7461-88

[51] Int. Cl.$^5$ ............................................. A61K 31/13
[52] U.S. Cl. ................................................... 514/663
[58] Field of Search ......................................... 514/663

[56] References Cited

U.S. PATENT DOCUMENTS 4,242,359 12/1980 Cooper et al. .................... 514/663

OTHER PUBLICATIONS

The Merck Index 10th edition (1983), p. 215.

Primary Examiner—Stanley J. Friedman
Assistant Examiner—Raymond J. Henley, III
Attorney, Agent, or Firm—Leydig, Voit & Mayer

[57] ABSTRACT

This invention relates to a treatment for the improvement of regeneration of injured striated muscles, the key-feature of which is the application of n-butylamine, in natural or ionic form or in buffered solution, as effective substance.

13 Claims, 3 Drawing Sheets

PREPARATION OF THE IMPROVEMENT OF THE REGENERATIVE PROCESS OF INJURED STRIATED MUSCLES

The present invention is related to the use of a therapeutic preparation to improve the regeneration of injured striated muscles. Under the influence of this treatment the reparative processes and formation of collagen are suppressed and an injured site regenerates by formation of new muscle fibers.

Until now, no treatment which would enable regeneration of injured striated muscles (incision, stab and lacerate wounds) was known. The injury of striated muscles heals by cicatrization, with the exception of special injury of a muscle as, such compression or application of some myotoxic local anesthetics, e.g. Marcain ® (bupivacaine). The scar is formed mostly by collagen and has no capacity to actively contract and from, the view of muscle activity, it presents only closing up of an injured site. Moreover, it is not aesthetic because it is formed by a mass of different optical properties and remains visible till the end of the life. In the above mentioned special cases of muscle injury, which are characterized by the injury being inside the muscle, without the loss of its total integrity, the activation of proliferation of satellite cells and formation of new muscle fibers takes place. These natural regenerative processes are activated if the muscle is injured mechanically to a great extent (incision, stab and lacerate wounds etc.) and within a fortnight they are fully substituted by a granular tissue which forms the scar.

The above mentioned failure in regeneration of injured striated muscles (incision, stab and lacerate wounds etc.) is solved by use of the preparation according to the invention, the key-feature of which is the presence of n-butylamine, in the form of either a free base or a physiologically acceptable salt or in buffered solution, as effective substance. The preparation is preferably applied in form of hydrochloride in water solution (saline), e.g. by injection into the vicinity of muscle injury. Use of the preparation suppresses reparative processes and formation of collagen and, by contrast, the regenerative processes develop fully, i.e. the proliferation of satellite muscle cells leads to the formation of new myotubes. At the site of injury a new muscle mass is formed i.e. a mass which possesses the same optical properties. After a certain time, the site of the original muscle injury is not visible.

By application of the preparation, the healing of the muscle injury is reached actually by a muscle mass and not by collagen, the formation of which is suppressed. The significance of this full-value regeneration is wide. Application in the treatment of muscle injury, both in veterinary and human practice, is made possible. Moreover, the treatment of muscle injury in humans is accompanied by an aesthetic factor in that no scars are formed in a muscle.

Examples of the results of the examination of an injured muscle using an optical microscope are mentioned in three enclosed figures. Both cases, i.e. a muscle healing without any intervention and a muscle healing after application of the preparation according to the invention, are described below:

FIG. 1: Histological section through the scar of injured muscle without application of the preparation. A scar formed by collagen (a) represents a normal way of healing. (Magnif. ×160).

Figure 2:

FIG. 2: Histological section through an injured muscle regenerating under the influence of the preparation. Regenerative changes of the muscle can be observed. The proliferation of satellite muscle cells followed by their differentiation leads to the formation of new myotubes (b). Collagen (a) occurs in numbers corresponding to uninjured muscle embedding of endomysium, formation of lamina basalis. (Magnif. ×160).

Figure 3:

FIG. 3: Detail of previous histological preparation. New myotubes are easily visible (b). (Magnif. ×450).

The invention is clarified in detail in example 1:

Fourteen 2-month-old rats weighing 280–285 g were used in the experiment. The injury to the 14 Musculus tybialis anterior was carried out on both hindlegs. The skin was cut with scissors, fascia was retracted aside and the muscle was injured by longitudinal and transverse incisions with fine scissors with sharp tips (incisions were 5 mm in length and 5 mm in depth). The skin was stitched and the injured site was immediately+ injected around with 0.37 ml solution of n-butylamine hydrochloride in saline (experimental) or with the same volume of saline (control). The volume was applied with 6 injections intramuscularly in the vicinity of the injured site.

+ both solutions were applied to rats no. 13 and 14 also on 5th and 9th day after injury The arrangement of the experiment was as follows:

| Rat no. | Applied | |
|---|---|---|
| | left leg | right leg |
| 1 | 0.37 ml of | 0.37 ml of |
| 2 | saline | saline |
| 3 | | |
| 4 | | |
| 5 | 0.37 ml | 0.37 ml of |
| 6 | 38 mg BU*/ml of saline | saline |
| 7 | 0.37 ml | 0.37 ml of |
| 8 | 76 mg BU/ml of | saline |
| 9 | saline | |
| 10 | | |
| 11 | 0.37 ml | 0.37 ml of |
| 12 | 152 mg BU/ml of saline | saline |
| 13 | 0.37 ml | 0.37 ml of |
| 14 | 76 mg BU/ml of saline after injury + on 5th and 9th day | saline after injury + on 5th and 9th day |

*BU = n-butylamine hydrochloride

The rats were killed and assessment of the healing process was made both visually and with the aid of an optic and electron microscope. The injuries around which were injected a solution of n-butylamine hydrochloride were healed with a new muscle mass; sometimes it was difficult to find the very site of injury. A total of 20 samples obtained from each studied muscle were taken for microscopic examination along the whole length of injury. It was confirmed that, in each case, where a solution of n-butylamine hydrochloride was applied in the vicinity of injury, regeneration of striated muscles, proliferation of satellite muscle cells and formation of new myotubes took place there. The formation of collagen was suppressed; only 5–20% of collagen was observed at the site of injury, whereas the remaining mass was formed especially by new myotubes. Injured right hind leg muscles of rats, in which n-butylamine hydrochloride penetrated only in low amounts through blood, and injured muscles of both hind legs of control rats no. 1–4, in which only saline was injected, healed in a classical manner, forming a collagen scar. Collagen represented 90–100% of the whole mass. New myotubes were found only sporadically and only a collagen scar was found in the middle of injury. It follows from the experiment that effects of concentration and repeated application were observed. The treatment shows a certain concentrative dependency; the region of optimum effect of the treatment can be determined, the effectiveness of the treatment being rather decreased at lower or higher concentrations. Application of the solution at a concentration of 76 mg of n-butylamine hydrochloride/ml of saline can be considered as optimum in the experiment. Repeated application (rats no. 13 and 14) improves regeneration.

This method offers the possibility of application both in veterinary and human practice during treatment of muscle injury. Another possible application is the suppression of reparative processes which favorably affect regeneration of other tissues than striated muscles.

We claim:

1. A method for improving regeneration of an injured striated muscle in a patient in need thereof comprising administering to said muscle in said patient a therapeutically effective amount of n-butyl amine.

2. The method according to claim 1 in which the n-butyl amine is in the form of either a free base or a physiologically acceptable salt or a mixture thereof.

3. The method according to claim 2 in which the physiologically acceptable salt of n-butyl amine is n-butyl amine hydrochloride.

4. The method according to claim 3 in which the effective amount of n-butyl amine hydrochloride is from about 14 mg to about 56 mg.

5. The method according to claim 4 in which the optimal effective amount of n-butyl amine hydrochloride is about 28 mg.

6. The method according to claim 1 in which the n-butyl amine is in aqueous solution.

7. The method according to claim 6 in which the aqueous solution is comprised of saline solution.

8. The method according to claim 6 in which the aqueous solution is comprised of buffers.

9. The method according to claim 1 in which the n-butyl amine is administered by injection into the vicinity of a muscle injury.

10. The method according to claim 9 in which the injection is intramuscular.

11. A method for improving the regeneration of an injured striated muscle in a patient in need thereof comprising administering to said muscle in said patient a therapeutically effective amount of n-butyl amine, by intramuscular injection of a saline solution comprised of about 28 mg of n-butyl amine hydrochloride.

12. The method according to claim 11 further comprising a second administration of n-butyl amine in the same manner as described for the first administration, said second administration occurring about 5 days after the time of injury to the striated muscle.

13. The method according to claim 12 further comprising a third administration of n-butyl amine, as described for the first and second administrations, said third administration occurring about 9 days after the time of injury to the striated muscle.

* * * * *